US00PP34379P2

(12) United States Plant Patent
Kolster et al.

(10) Patent No.: US PP34,379 P2
(45) Date of Patent: Jun. 28, 2022

(54) ***HYDRANGEA* PLANT NAMED 'HOKOMABURLAC'**

(50) Latin Name: *Hydrangea macrophylla*
Varietal Denomination: Hokomaburlac

(71) Applicants: Kolster Holding B.V., Boskoop (NL); Horteve Breeding B.V., Aalsmeer (NL)

(72) Inventors: Peter Rudolf Kolster, Boskoop (NL); Cornelis Pieter Eveleens, Aalsmeer (NL)

(73) Assignees: Horteve Breeding BV, Aalsmeer (NL), Part Interest; Kolster Holding BV, Boskoop (NL), Part Interest ( * ) Notice: Subject to any disclaimer, the term of this patent is extended or adjusted under 35 U.S.C. 154(b) by 0 days.

(21) Appl. No.: 17/505,501

(22) Filed: Oct. 19, 2021

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 6/48; A01H 5/02
See application file for complete search history.

*Primary Examiner* — Keith O. Robinson
(74) *Attorney, Agent, or Firm* — Penny J. Aguirre

(57) ABSTRACT

A new cultivar of *Hydrangea macrophylla* plant named 'Hokomaburlac' that is characterized by its dark colored leaves, its inflorescences with sterile sepals that are dark red in color, its very sturdy flowers, and its suitability for use as a potted plant and for cut flowers.

2 Drawing Sheets

Botanical classification: *Hydrangea macrophylla.*
Varietal denomination: 'Hokomaburlac'.

BACKGROUND OF THE INVENTION

The present invention relates to a new and distinct cultivar of *Hydrangea macrophylla* and will be referred to hereafter by its cultivar name, 'Hokomaburlac'. 'Hokomaburlac' represents a new mophead type *Hydrangea*, a deciduous shrub grown for use as a landscape plant.

'Hokomaburlac' was derived from an ongoing breeding program conducted by the Inventors in Boskoop, The Netherlands. The objectives of the breeding program are to develop a new cultivar of *Hydrangea macrophylla* with red inflorescences combined with other desirable characteristics.

The Inventors made a controlled cross in June of 2013 in Boskoop, The Netherlands between 'Mysterious' female parent (U.S. Plant Pat. No. 32,970) and an unnamed and unpatented plant from the Inventors' breeding program as the male parent (ref. code 11-010-007). 'Hokomaburlac' was selected in June of 2015 as a single unique plant amongst the resulting seedlings.

Asexual propagation of the new cultivar was first accomplished under the direction of the Inventors by stem cuttings in August of 2015 in Boskoop, The Netherlands. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Hokomaburlac' as a unique cultivar of *Hydrangea.*

1. 'Hokomaburlac' dark colored leaves.
2. 'Hokomaburlac' exhibits inflorescences with sterile sepals that are dark red in color.
3. 'Hokomaburlac' exhibits very sturdy flowers.
4. 'Hokomaburlac' exhibits suitability for use as a potted plant and for cut flowers.

The female parent of 'Hokomaburlac' differs from 'Hokomaburlac' in having inflorescences that are less sturdy and sterile flower sepals that are more green in color with margins that are smoother. The male parent of 'Hokomaburlac' differs from 'Hokomaburlac' in having inflorescences that are less sturdy with sterile flower sepals that are lighter red and more green in color. 'Hokomaburlac' can be most closely compared to the *Hydrangea macrophylla* cultivars 'Kolmadaru' (not patented) and 'Hokomaginfe' (not patented). 'Kolmadaru' is similar to 'Hokomaburlac' in having dark green colored leaves and sterile flower sepals that are red in color. 'Kolmadaru' differs from 'Hokomaburlac' in having inflorescences that are less sturdy, a much better re-blooming habit, and lighter colored green leaves. 'Hokomaginfe' is similar to 'Hokomaburlac' in having dark colored leaves, suitability for as a potted plant and for cut flowers, and sterile flower sepals that are red in color. 'Hokomaginfe' differs from 'Hokomaburlac' in having darker colored leaves and sterile flower sepals that are red, white and green in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosure includes but may not be limited to a website listings by Floraldaily.

BRIEF DESCRIPTION OF THE DRAWINGS

The accompanying color photographs illustrates the overall appearance and distinct characteristics of the new *Hydrangea*. The photographs were taken of a two-year-old plant as grown outdoors in a 2-gallon container in Abbotsford, British Columbia, Canada.

The photograph in FIG. 1 provides a side view of the plant habit of 'Hokomaburlac' with inflorescence buds.

Figure 1:
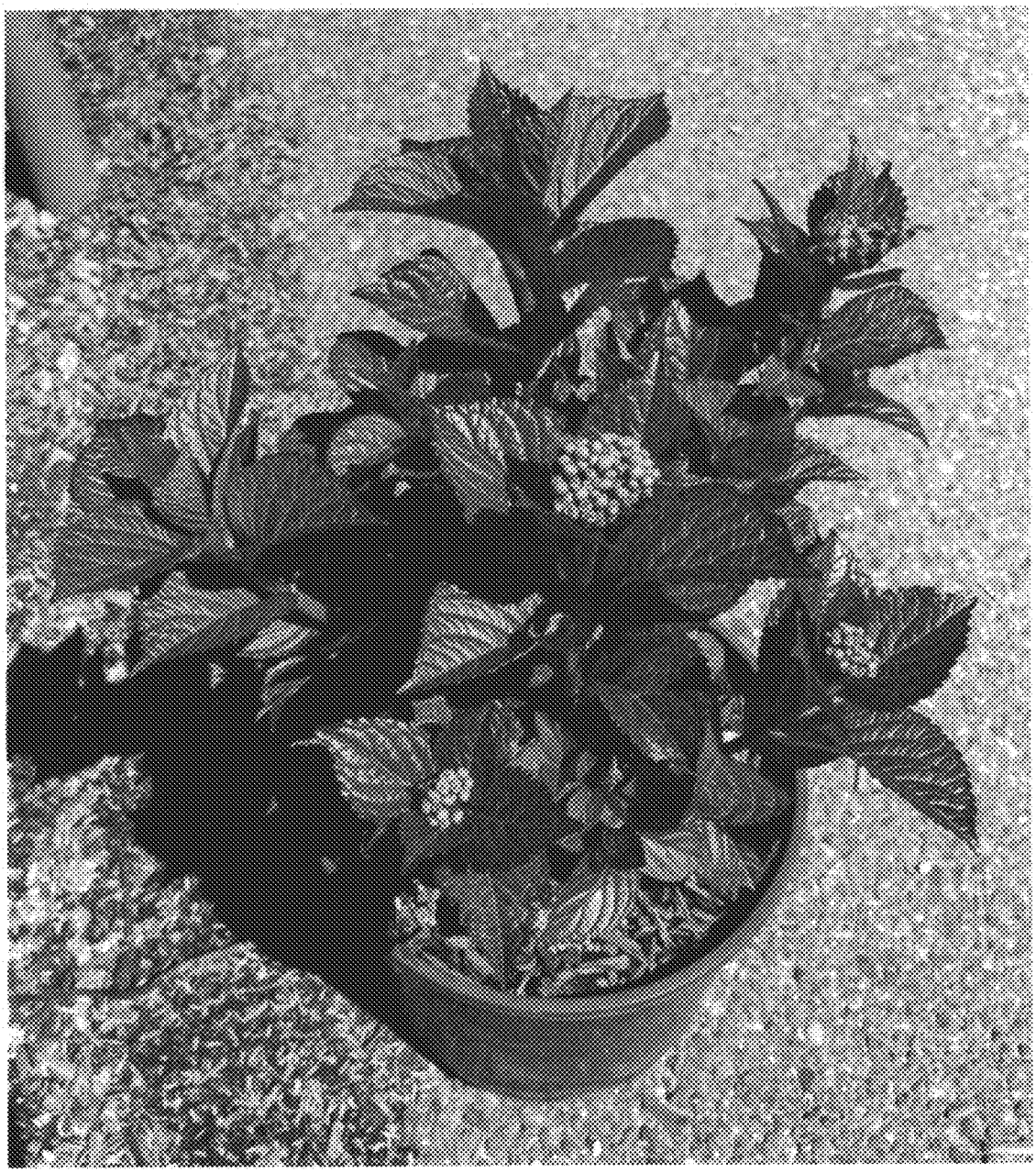
Figure 2:
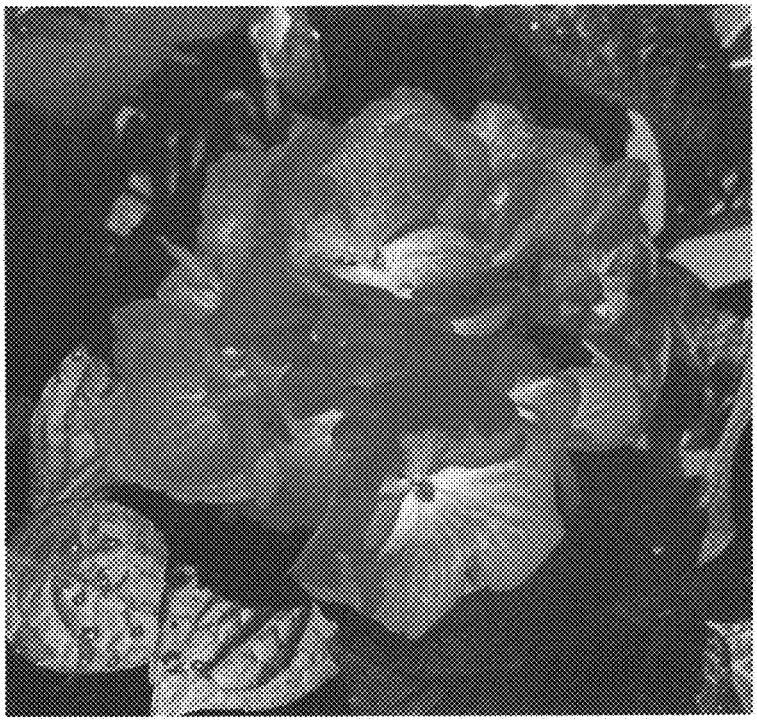

The photograph in FIG. 2 provides a close-up view of an inflorescence of 'Hokomaburlac'.

Figure 3:
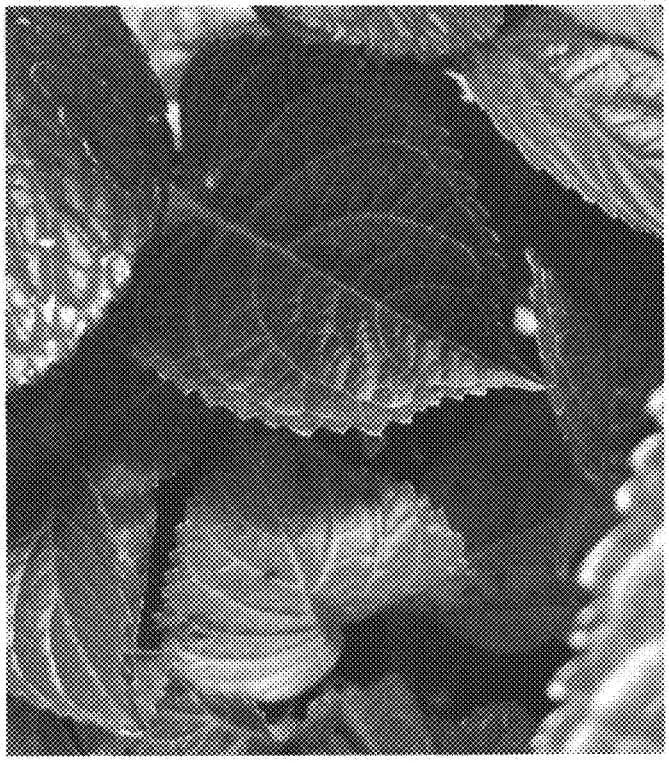

The photograph in FIG. 3 provides a close-up view of the foliage of 'Hokomaburlac'.

The colors in the photographs may differ slightly from the color values cited in the detailed botanical description, which accurately describe the colors of the new *Hydrangea*.

BOTANICAL DESCRIPTION OF THE PLANT

The following is a detailed description of two-year-old plants of 'Hokomaburlac' as grown outdoors in 2-gallon containers in Abbotsford, British Columbia, Canada. The phenotype of the new cultivar may vary with variations in environmental, climatic, and cultural conditions, as it has not been tested under all possible environmental conditions. The plants were grown under non-blueing conditions and blueing conditions have not been tested. The color determination is in accordance with The 2015 Colour Chart of The Royal Horticultural Society, London, England, except where general color terms of ordinary dictionary significance are used.

General description:

*Blooming period.*—At least 2 months, summer through autumn in The Netherlands.

*Plant type.*—Deciduous shrub, mophead type *Hydrangea.*

*Plant habit.*—Compact, suitable for container growing, sturdy stems and flowers.

*Height and spread.*—Reaches about 38 cm in height and 31 cm in spread as grown in a 2-gallon container, reaches 1 m in height and width as grown as a 3-year-old plant in the landscape.

*Hardiness.*—At least to U.S.D.A. Zones 5 to 9.

*Diseases and pests.*—No resistance or susceptibility to diseases or pests has been observed.

*Root description.*—Fine and fibrous, NN155B in color.

*Propagation.*—Softwood stem cuttings.

*Growth rate.*—Moderate.

*Root development.*—Time required for root initiation is about 6 weeks, time required to produce a young plant from rooted cutting is about 18 weeks.

Stem description:

*Stem shape.*—Rounded.

*Stem strength.*—Very strong.

*Stem color.*—Young and mature; 144A in color, mature bark; color is a blend of 199A and N200A.

*Stem size.*—Main branches; average of 10 cm in length, 6 mm in diameter, lateral branches; average of 6 cm in length and 4 mm in diameter.

*Stem surface.*—Younger and mature stems; glabrous and slightly glossy, lenticellate, lenticles; sparse 7 per $cm^2$, an average of 0.75 mm in length and 0.3 mm in width, 200C in color, old growth at base; bark-like, mostly smooth and can be slightly exfoliating.

*Internode length.*—Average of 3 cm.

*Branching.*—Average of 6 main branches, average of 3 lateral branches per main branch.

*Stipules.*—Persistent, 2 opposite at base of petioles, stipule bud; is 1.5 mm in length, 0.5 mm in width, 187A in color on both surfaces, oblong in shape, acute apex, matte on both surfaces.

Foliage description:

*Leaf shape.*—Elliptical.

*Leaf arrangement.*—Opposite and slightly whorled.

*Leaf division.*—Simple.

*Leaf base.*—Attenuate.

*Leaf apex.*—Apiculate.

*Leaf margins.*—Serrate.

*Leaf venation.*—Pinnate, young upper and lower surface; 145A, mature upper surface; a blend of 160A and N144A, flushed with 178A, mature lower surface a 193A.

*Leaf size.*—Average of 8.5 cm in length and 7 cm in width.

*Leaf attachment.*—Petiolate.

*Leaf surface.*—Upper and lower surface glossy.

*Leaf color.*—Young upper surface; a blend of NN137A and 144A, young lower surface; 138A, mature upper surface; 147A, later becoming flushed with 183A starting at the tip and margins and expanding to most of the leaf, mature lower surface; 143B, mottled with 200A around the margins and outer regions, older and fall leaves upper surface; an irregular blend of 183A, 45A, and 2D, tips 202A, older and fall leaves lower surface; 160C, mottled with 200A around the margins and outer regions.

*Petioles.*—An average of 7 mm in length and 4 mm in diameter, both surfaces slightly glossy, young color; 145A, mature color; 145A, flushed with 178B.

Inflorescence description:

*Inflorescence type.*—Terminal panicle, full rounded mophead in form, comprised of single sterile flowers and inconspicuous fertile flowers.

*Lastingness of inflorescence.*—Persistent at least 2 months in color.

*Inflorescence number.*—One per lateral.

*Inflorescence size.*—Average of 5 cm in height, 7 cm in diameter.

*Flower number.*—Average of 25 sterile flowers and 13 fertile flowers per panicle.

*Flower fragrance.*—None.

*Flower aspect.*—Upright to outward.

*Flower size.*—Sterile flowers; an average of 3 cm in diameter, 1 cm in depth, fertile flowers; an average of 9 mm in diameter and 5 mm in depth.

*Flower type.*—Rotate.

*Flower buds.*—Sterile flowers; average of 5 mm in length and diameter, rounded, globular in shape, color; young buds 144A, maturing buds a blend of 145A and 182B, fertile flowers; average of 4 mm in length and 3 mm in diameter, globular in shape, color; young buds 144A, maturing buds 142B.

*Peduncles.*—Moderately strong, average of 1 cm in length and 3 mm in width, color; 144A, with random blotches of 187A, surface is matte, smooth.

*Pedicels.*—Moderately strong, average of 6 mm in length and 2 mm in width, color; young and mature pedicels 144A, occasionally speckled with 187A in color, and moderately covered with very fine woolly hairs that match surface color.

*Petals.*—Sterile flowers; 5, rotate, 3 mm in length, 2 mm in diameter, obovate in shape, acute apex, cuneate base, entire margins, cup-shaped, glabrous and matte surface, colors; when opening and fully open upper surface (inner surface) NN78A, margins and tip NN155D, when opening and fully open lower surface (outer surface) NN78C, margins and tip NN155D, fertile flowers; 5, rotate, 4 mm in length, 3 mm in width, linear in shape, acute apex, cuneate base, entire margins, cup-shaped, glabrous and matte surface, color; young outer surface 144A, young inner surface NN74A, margins 75D, mature inner and outer surface; NN74A, margins 75D.

*Sepals.*—Sterile flowers; showy, 5, deltoid to reniform in shape, moderately to strongly overlapping, rotate in arrangement, entire margins moderately undulate, apex is very slightly retuse to bluntly pointed, cuneate base, average of 1.3 cm in length and 1.7 cm in width, upper and lower surface glabrous and satiny, color: when initially opening upper and lower surface; 143A, when opening upper and lower surface; base 73A, centers 12C with streaks of 143A, margins and tips 73A and outer most edges 61A, when fully open upper surface; a blend of 64A and 64D, when fully open lower surface; 65D, veins 71A, fertile flowers; 6, rotate in arrangement, ovate to broadly ovate in shape, entire margins, acute apex, cuneate base, average of 1.5 mm in length and 2 mm in width, both surfaces are glabrous, color; young and mature upper and lower surface 144B, tips 144A.

Reproductive organs:

*Stamens.*—Sterile flowers; average of 10, anther is reniform in shape, 2-parted, 0.5 mm in diameter, young color 1B, mature color 13A, filament is 4 mm in length, 1 mm in width and NN155C in color, pollen is low in quantity and 10D in color, fertile flowers; average of 9, anther is reniform in shape, 2-parted, 1.2 mm in length, 1 mm in width and young color 145B, mature color N144A, filament is 4 mm in length and NN155B in color, pollen is low in quantity and too small amount for color reading.

*Pistils.*—Sterile flowers; average of 2, an average of 2 mm in length, stigma is club-shaped, 1 mm in diameter and 155A in color, style is 158C in color, ovary is 1 mm in diameter, 158A in color and inferior, fertile flowers; average of 3, an average of 2 mm in length, stigma is clavate in shape and 150D in color, style is 150D in color, ovary is 1 mm in diameter, N148A in color and inferior.

*Fruit and seed.*—None observed to date.

It is claimed:

1. A new and distinct cultivar of *Hydrangea* plant named 'Hokomaburlac' substantially as herein illustrated and described.

* * * * *